United States Patent [19]

Soubrie et al.

[11] Patent Number: 5,043,352
[45] Date of Patent: Aug. 27, 1991

[54] CHROMAN DERIVATIVES FOR THE TREATMENT OF DEPRESSIVE STATES

[75] Inventors: Philippe Soubrie; Martine Poncelet, both of Montpellier, France

[73] Assignee: Sanofi, Paris, France

[21] Appl. No.: 440,328

[22] Filed: Nov. 22, 1989

[30] Foreign Application Priority Data

Nov. 23, 1988 [FR] France ................ 88 15283

[51] Int. Cl.$^5$ ............................. A01N 43/16
[52] U.S. Cl. ................................. 514/456
[58] Field of Search ........................ 514/456

[56] References Cited

U.S. PATENT DOCUMENTS

| Re. 30,739 | 9/1981 | Gardner | 260/345.2 |
| 4,080,335 | 3/1978 | Gardner | 260/345.2 |
| 4,146,539 | 3/1979 | Gardner | 546/196 |
| 4,148,909 | 4/1979 | Gardner | 424/283 |
| 4,780,478 | 10/1988 | Hausberg et al. | 514/456 |

FOREIGN PATENT DOCUMENTS

| 076075 | 4/1983 | European Pat. Off. . |
| 091748 | 10/1983 | European Pat. Off. . |
| 093535 | 11/1983 | European Pat. Off. . |
| 120426 | 10/1984 | European Pat. Off. . |
| 273262 | 7/1988 | European Pat. Off. . |

Primary Examiner—Stanley J. Friedman
Assistant Examiner—T. Criares
Attorney, Agent, or Firm—Bacon & Thomas

[57] ABSTRACT

A method of treatment of depressive states which comprises administering in mammals in need thereof an effective amount of a compound

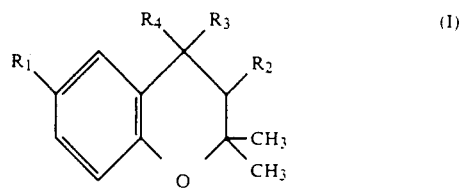

(I)

$R_1$ represents hydrogen, a halogen atom, a cyano group a nitro group, an acetyl group or a trifluoromethyl group;

$R_2$ represents a hydroxyl group, in which case $R_3$ represents a hydrogen atom, or $R_2$ and $R_3$ taken together represent an additional bond between the carbon atoms by which they are carried; and $R_4$ represents a 2-oxopyrrolidin-1-yl or 2-oxopiperid-1-yl group or a heterocyclic group selected from 1H-pyrid-2-on-1-yl, 1H-pyridazin-6-on-1-yl, 1H-pyrimidin-2-on-1-yl, 1H-pyrimidin-6-on-1-yl, 1H-pyrazin-2-on-1-yl and 1H-thiopyrid-2-on-1-yl groups which are unsubstituted or monosubstituted or disubstituted by a $C_1$-$C_4$ alkyl group, a halogen atom or a hydroxyl, nitro, amino or carboxyl group and the pharmaceutically acceptable salts thereof.

4 Claims, No Drawings

CHROMAN DERIVATIVES FOR THE TREATMENT OF DEPRESSIVE STATES

The present invention relates to the use of chroman derivatives for the preparation of pharmaceutical compositions for combating depression, to a method for the treatment of depressive states using said chroman derivatives, and to pharmaceutical compositions for the treatment of depression.

In recent years, the European patent applications published under the numbers 76 075, 91 748, 93 535, 120 426 and 273 262 have described families of chroman-3-ol and 2H-chromene derivatives which share an antihypertensive activity.

These chroman-3-ol and 2H-chromene compounds are also described in U.S. Pat. Nos. 4,446,113, 4,542,149, 4,644,070, and 4,555,509.

The present invention relates to the use of chromanol or chromene derivatives for the treatment of depressive states in mammals in need thereof.

According to the present invention, the compounds of formula (I) below and the pharmaceutically acceptable salts thereof, can be used for the treatment of depression:

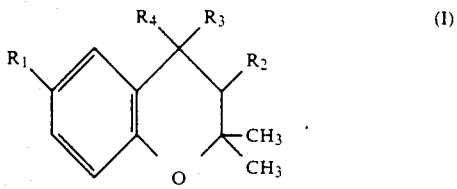

In this formula, $R_1$ represents hydrogen, a halogen atom, a cyano group, a nitro group, an acetyl group or a trifluoromethyl group;

$R_2$ represents a hydroxyl group, in which case $R_3$ represents a hydrogen atom, or $R_2$ and $R_3$ taken together represent an additional bond between the carbon atoms by which they are carried; and $R_4$ represents a 2-oxopyrrolidin-1-yl or 2-oxopiperid-1-yl group or a heterocyclic group selected from 1H-pyrid-2-on-1-yl, 1H-pyridazin-6-on-1-yl, 1H-pyrimidin-2-on-1-yl, 1H-pyrimidin-6-on-1-yl, 1H-pyrazin-2-on-1-yl nd 1H-thiopyrid-2-on-1-yl groups which are unsubstituted r monosubstituted or disubstituted by a $C_1$–$C_4$ alkyl group, a halogen atom or a hydroxyl, nitro, amino or carboxyl group.

Examples of such compounds are given in the published European patent applications cited above.

The compounds of formula (I) in which $R_2$ is a hydroxyl are asymmetric, so they can exist in the form of optical isomers. The present invention relates to the individual isomers as well as to mixtures thereof or the racemic compounds.

The compounds of formula (I) can be prepared as described in the European patent applications and U.S. patents cited above or by analogous methods.

The compounds of formula (I) can be administered orally, sublingually, subcutaneously or parenterally.

The amount of active principle to be administered for the treatment of depressive states depends, in conventional manner, on the nature and severity of the complaints to be treated and on the weight of the patients. However, the dosage units will normally contain from 5 to 500 mg of active ingredient in combination with a pharmaceutical excipient.

This unit dose can be administered from once to 5 times per day, resulting in a daily dosage of 25 to 2500 mg and preferably of 50 to 1500 mg.

In the pharmaceutical compositions of the present invention for oral, sublingual, subcutaneous, intramuscular, intravenous or rectal administration, the active principles of formula (I) above, or salts thereof if desired, can be administered to humans in unit dosage forms of administration, mixed with conventional pharmaceutical excipients, for the prophylaxis or treatment of the above disorders or diseases. The appropriate unit dosage forms of administration include forms for oral administration, such as tablets, capsules, powders, granules and solutions or suspensions to be taken orally, forms for sublingual administration, forms for subcutaneous, intramuscular or intravenous administration and forms for rectal administration.

When a solid composition is prepared in the form of tablets, the principal active ingredient is mixed with a pharmaceutical vehicle such as gelatin, starch, lactose, magnesium stearate, talc, gum arabic or the like. The tablets can be coated with sucrose, a cellulose derivative or other appropriate substances, or they can be treated in such a way that they have a sustained or delayed activity and release a predetermined amount of active principle continuously.

A preparation in the form of capsules is obtained by mixing the active ingredient with a diluent and pouring the resulting mixture into soft or hard capsules.

A preparation in the form of a syrup or an elixir or for administration in the form of drops may contain the active ingredient in combination with a sweetener, which is preferably calorie-free, methylparaben and propylparaben as antiseptics, a flavoring agent and an appropriate dye.

Water-dispersible granules or powders may contain the active ingredient mixed with dispersants or suspension agents, such as polyvinylpyrrolidone, as well as with sweeteners or taste correctors.

Rectal administration is carried out using suppositories, which are prepared with binders melting at the rectal temperature, for example cacao butter or polyethylene glycols.

Parenteral administration is carried out using aqueous suspensions, isotonic saline solutions or sterile and injectable solutions which contain pharmacologically compatible dispersants and/or wetting agents, for example propylene glycol or butylene glycol.

The active principle may also be formulated as microcapsules, with one or more excipients or additives if desired.

The pharmacological results reported below illustrate the activity of compounds of formula (I) in an indicative test for compounds of potential use in the treatment of depressive states.

The compounds tested are as follows:

Compound 1: Trans-6-cyano-2,2-dimethyl-4-(2-oxopyrrolidin-1-yl)chroman-3-ol

Compound 2: Trans-6-cyano-2,2-dimethyl-4-(1H-2-oxopyrid-1-yl)chroman-3-ol

Compound 3: Trans-6-cyano-2,2-dimethyl-4-(4-chloro-1H-2-oxopyrid-1-yl)chroman-3-ol Compound 4: Trans-6-cyano-2,2-dimethyl-4-(1H-6-oxopyridazin-1-yl)chroman-3-ol Compound 5: Trans-6-cyano-2,2-dimethyl-4-(3-hydroxy-1H-6-oxopyridazin-1-yl)chroman-3-ol Compound 6: Trans-2,2-dimethyl-4-(1H-2-oxopyrid-1-yl)chroman-3-ol Compound 7: 6-Cyano-2,2-dimethyl-4-(1H-2-oxopyrid-1-yl)-2H-chromene Compound 8: 6-Acetyl-2,2-dimethyl-4-(1H-2-oxopyrid-1-yl)-2H-chromene Compound 9: 6-Bromo-2,2-dimethyl-4-(1H-2-oxopyrid-1-yl)-2H-chromene Compound 10: 6-Amino-2,2-dimethyl-4-(1H-2-oxopyrid-1-yl)-2H-chromene Compound 11: Trans-6-cyano-2,2-dimethyl-4-(1H-2-oxopyrid-1-yl)chroman-3-ol, levorotatory isomer Compound 12: 6-Bromo-2,2-dimethyl-4-(1,2-dihydro-2-oxopyrid-1-yl)chromene Compound 11 was prepared from the corresponding racemic compound, compound 2, using a known method: an optically active carbamic acid ester is prepared as an intermediate by the method described in European patent application No.120 428:

Preparation of compound 11:

A mixture containing 6.5 g of compound 2, 180 ml of toluene and 6 g of S(−)-α-methylbenzyl isocyanate is refluxed for 24 hours. It is concentrated under vacuum and the residue is taken up with 300 ml of ethyl ether. The insoluble material is filtered off and then crystallized from 160 ml of ethyl acetate to give 1 g of product. This is then recrystallized twice from an ethyl acetate/pentane mixture (1/1) to give 0.8 g of the α-methylbenzyl carbamate.

Melting point: 280° C.

$\alpha_D^{23}$: −8.5(acetone, C=1).

A mixture containing 0.7 g of the compound obtained above, 3 ml of chloroform, 1.5 ml of triethylamine and 1.4 ml of 95% trichlorosilane is stirred for 24 hours. It is poured on to ice and then extracted with chloroform, the insoluble material is filtered off and the product is treated with hot methanol. The organic phase is concentrated under vacuum to give 0.9 g of a solid. This is chromatographed on a silica column, using a methylene chloride/ethyl acetate mixture (7/3) as the eluent, to give 0.4 g of the expected product.

Melting point: 260°–265° C.

$\alpha_D^{23}$: −43.0(chloroform, C=1).

Analysis of the IR and NMR spectra confirms the structure.

Porsolt's test: The products according to the invention were subjected to the forced swimming test according to Porsolt et al. (Archives Internationales de Pharmacodynamie, 1977, 229, 327–336).

Female mice (Iffa Credo) weighing 22 to 24 g are immersed for a period of 6 minutes in a beaker containing 800 ml of water at 24°±1° C.

In the absence of treatment, the animals adopt a characteristic immobile posture after a brief period of activity. The immobility is reduced by substances exhibiting an antidepressant activity, whereas tranquilizers have no effect.

The products to be studied are administered intraperitoneally at a rate of 10 animals per dose and the animals are subjected to the test 30 minutes later. The immobility times are measured over 4 minutes from the 2nd to the 6th minute of the experiment.

The results are expressed as the percentage variation of the immobility time relative to a group of untreated control animals.

The results obtained are collated in the Table below:

| Product | Dose mg/kg i.p. | % variation in immobility time |
|---|---|---|
| Compound 1 | 0.25 | −26** |
| Compound 2 | 0.5 | −24** |
|  | 2 | −30*** |
| Compound 3 | 0.06 | −25* |
| Compound 4 | 0.25 | −31* |
| Compound 5 | 0.5 | −27* |
| Compound 6 | 1 | −13* |
| Compound 7 | 0.125 | −21*** |
|  | 0.25 | −32*** |
|  | 0.5 | −44*** |
| Compound 8 | 0.25 | −28** |
| Compound 9 | 0.03 | −22* |
|  | 0.125 | −35** |
| Compound 10 | 1 | −36** |
| Compound 11 | 1 | −40** |
| Compound 12 | 0.125 | −35* |

Student t test
*p < 0.05
**p < 0.01
***p < 0.001

What is claimed is:

1. The method of treatment of depressive states which comprises administering to a mammal in need thereof an effective amount of a compound of formula:

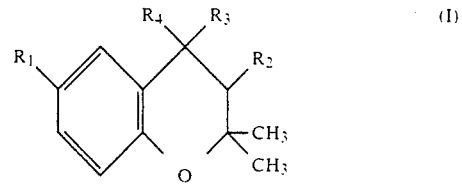

in which:

R$_1$ represents hydrogen, a halogen atom, a cyano group, a nitro group, an acetyl group or a trifluoromethyl group;

R$_2$ represents a hydroxyl group, in which case R$_3$ represents a hydrogen atom, or R$_2$ and R$_3$ taken together represent an additional bond between the carbon atoms by which they are carried; and R$_4$ represents a 2-oxopyrrolidin-1-yl or 2-oxopiperid-1-yl group or a heterocyclic group selected from 1H-pyrid-2-on-1-yl, 1H-pyridazin-6-on-1-yl, 1H-pyrimidin-2-on-1-yl, 1H-pyrimidin-6-on-1-yl, 1H-pyrazin-2-on-1-yl and 1H-thiopyrid-2-on-1-yl groups which are unsubstituted or monosubstituted or disubstituted by a C$_1$–C$_4$ alkyl group, a halogen atom or a hydroxyl, nitro, amino or carboxyl group and the pharmaceutically acceptable salts thereof with a pharmaceutically acceptable excipient.

2. The method of claim 1, wherein R$_2$ represents a hydroxyl and R$_3$ is hydrogen.

3. The method of claim 1, wherein R$_2$ and R$_3$ taken together form a bond.

4. The method of claim 1, wherein the compound of formula (I) is selected from: trans-6-cyano-2,2-dimethyl-3-hydroxy-4-(4-chloro-1H-2-oxopyrid-1-yl)chroman and 6-cyano-2,2-dimethyl-4-(1H-2-oxopyrid-1-yl)-2H-chromene.

* * * * *